United States Patent [19]

Lukase et al.

[11] Patent Number: 5,044,954
[45] Date of Patent: Sep. 3, 1991

[54] FORCEPS WITH INSERTS FOR REMOVING A DENTAL CROWN AND BRIDGE

[75] Inventors: Stephen P. Lukase, Glendale, Ariz.; Thomas A. Lukase, 2670 Greentree La., La Jolla, Calif. 92037

[73] Assignee: Thomas A. Lukase, Glendale, Ariz.

[21] Appl. No.: 601,663

[22] Filed: Oct. 23, 1990

[51] Int. Cl.$^5$ .................................................. A61C 3/16
[52] U.S. Cl. .................................................. 433/159
[58] Field of Search ............................... 433/159, 160

[56] References Cited

U.S. PATENT DOCUMENTS

| 831,307 | 9/1906 | Spahn | 433/160 |
|---|---|---|---|
| 2,674,800 | 4/1954 | Osborn et al. | 433/159 |
| 3,898,738 | 8/1975 | Linder | 433/159 |
| 4,197,647 | 4/1980 | Goldenthal | 433/159 |

Primary Examiner—John J. Wilson
Attorney, Agent, or Firm—Cahill, Sutton & Thomas

[57] ABSTRACT

A pair of dental forceps, whether configured for anterior, premolar or molar teeth, includes a pair of jaw mounted removable cushioning and gripping inserts for conformingly gripping and frictionally retaining a respective dental prosthetic device, such as a crown, to be removed without imposing stress concentrations sufficient to mar or damage the dental prosthetic device.

16 Claims, 2 Drawing Sheets

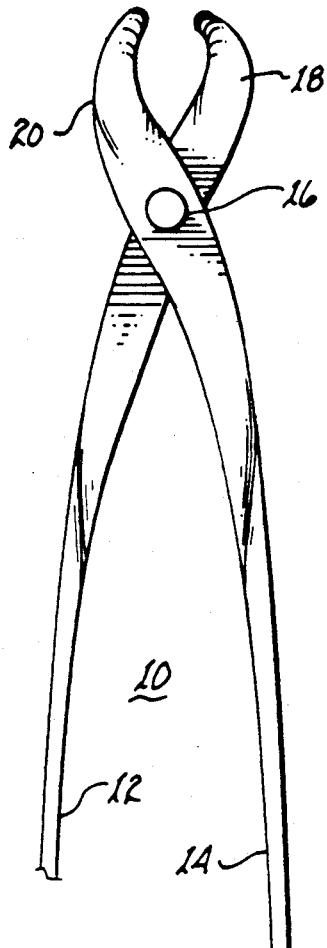
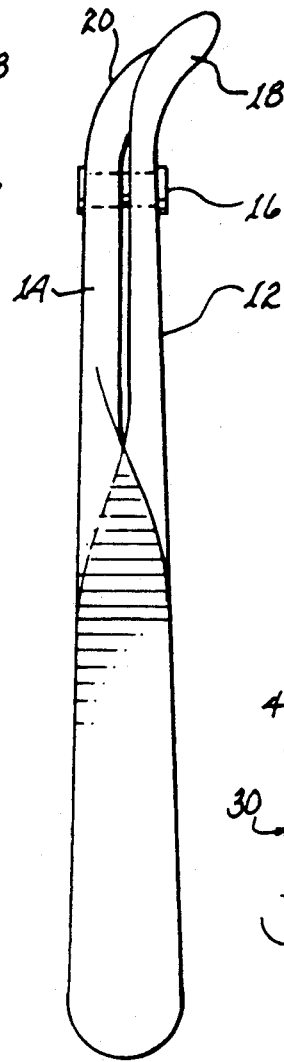
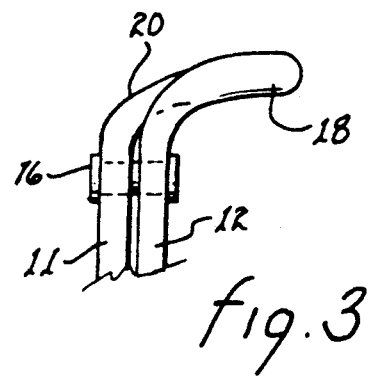
fig.3
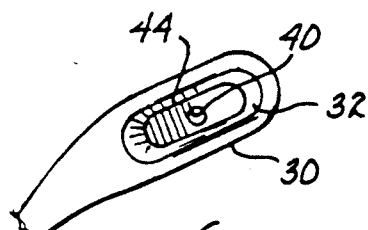
fig.4
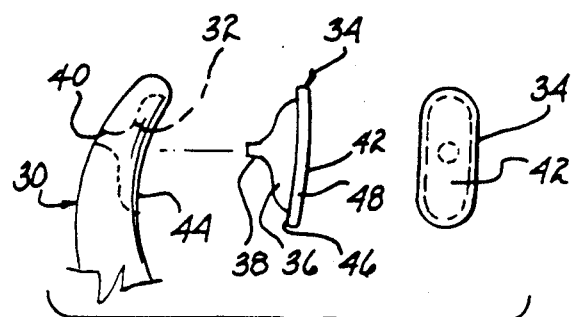
fig.5
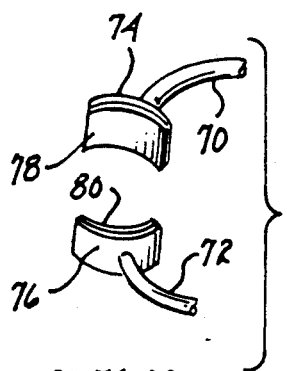
fig.8 PRIOR ART
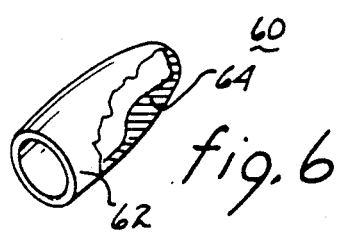
fig.6
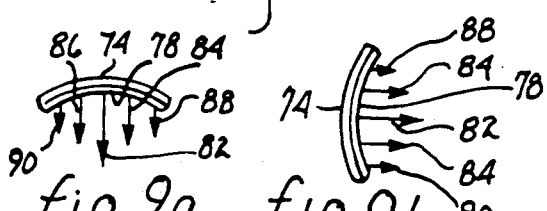
fig.9a  fig.9b  fig.7a  fig.7b
PRIOR ART

FORCEPS WITH INSERTS FOR REMOVING A DENTAL CROWN AND BRIDGE

BACKGROUND OF THE INVENTION

1. Field of the Invention

The present invention relates to dental implements and, more particularly, to forceps for removing dental prosthetic devices.

2. Description of the Prior Art

Dental forceps, particularly configured for use upon the anterior, premolar or molar teeth have been available for years for purposes of extracting a tooth. These forceps have jaws particularly angled and of a length to facilitate grasping a particular tooth. During tooth extraction, it is very important that a firm grip of the tooth be achieved and it is of no consequence if the enamel of the tooth cracks or if the tooth is otherwise damaged.

The forceps used for extracting teeth have been developed over a period of many decades to provide an effective combination of gripping a tooth and ease of manipulation of the gripped tooth to effect the extraction process. Primarily, the developmental work has been directed to the length and angulation of the gripping jaws.

To remove a crown for purposes of reattaching it more securely to develop a better seal or for adjustment purposes, it is very important that the crown not be aesthetically damaged or physically distorted. To use a conventional pair of extraction forceps for this purpose presents a real problem for the following reasons. The jaws of the forceps may damage the surface of the crown even though a good firm grip is established. If the forceps are only lightly squeezed to avoid damage to the crown, the jaws may slip from the crown and cause injury to the patient or damage to other teeth or restorations. For these reasons, many dentists use their fingers, and particularly their fingernails, to grasp the cervical ridge of the crown to dislodge and extract the crown. Since not all dentists have sufficient power in their fingers for this purpose, crown removal is a problem. Similarly, not all dentists have sufficiently robust fingernails to withstand the forces imposed without bending and causing substantial pain to the dentist. A potential problem of fungal infection also exists.

Various devices have been developed over the years to attempt to solve the above enumerated problems. In the 1920s, a clamp forceps was developed which cooperated with a detachably attached rubber dam to minimize damage to a crown while retaining sufficient gripping and extracting force. Regrettably, this device was difficult and awkward to use as a practical matter. Some time later, a pair of forceps was developed which included a pair of opposed curved surfaces lined with resilient material for gripping a crown. These forceps were very difficult to use for all teeth due to the different requirements of grip and manipulation imposed by the placement of each tooth within the mouth.

A yet further device was developed which is of a plier like configuration having one jaw of the pair of jaws oriented to contact and bear against the proximal edge of the crown while the second jaw was penetrably inserted through a passageway cut in the top of the crown to bear against the underlying tooth. In situations where the underlying tooth is little more than a post, this device is ineffective. Moreover, the requirement for a passageway through the cusp of the crown necessitated repair and reconstruction of the crown prior to remounting.

SUMMARY OF THE INVENTION

A pair of extraction forceps, configured in correspondence with the tooth supporting a crown to be removed includes removable inserts disposed in the jaws for gripping with sufficient force to permit removal of the crown while preventing damage or disfigurement to the crown surface and structure. The replaceabilty of the inserts permits autoclaving or other sterilizing procedures of the forceps and inserts may be disposable after one use. Moreover, the forceps with inserts are readily useable for extracting bridges and other dental prosthetic devices which may need adjustment, repair or reconstruction without causing damage during such extraction.

It is therefore a primary object of the present invention to provide a pair of forceps for grasping and removing a dental prosthetic device without damaging it.

Another object of the present invention is to provide resilient conformable inserts for the jaws of a pair of forceps to grasp and remove a crown.

A further object of the present invention is to provide removable inserts for use with dental forceps to extract dental prosthetic devices.

A still further object of the present invention is to provide a method for extracting a dental prosthetic device without damaging the device during extraction.

A yet further object of the present invention is to provide a method for firmly grasping but not damaging a dental crown to be removed.

These and other objects of the present invention will become apparent to those skilled in the art as the description thereof proceeds.

BRIEF DESCRIPTION OF THE DRAWINGS

The present invention will be described with greater clarity and specificity with reference to the following drawings, in which:

FIG. 1 is a partial plan view of a pair of forceps;

FIG. 2 is a side view of the pair of forceps shown in FIG. 1;

FIG. 3 illustrates a variant of the jaw configuration of the forceps shown in FIG. 2;

FIG. 4 illustrates an insert disposed in one of the jaws of the pair of forceps;

FIG. 5 is an exploded view illustrating the shape and placement of an insert within a jaw of a pair of forceps;

FIG. 6 illustrates a boot usable with each jaw of the pair of forceps;

FIGS. 7a and 7b depict the force vectors acting upon the crown;

FIG. 8 illustrates a prior art crown engaging device;

FIGS. 9a and 9b depict the force vectors attendant the device shown in FIG. 8;

DESCRIPTION OF THE PREFERRED EMBODIMENT

Figures 10A, 10B:
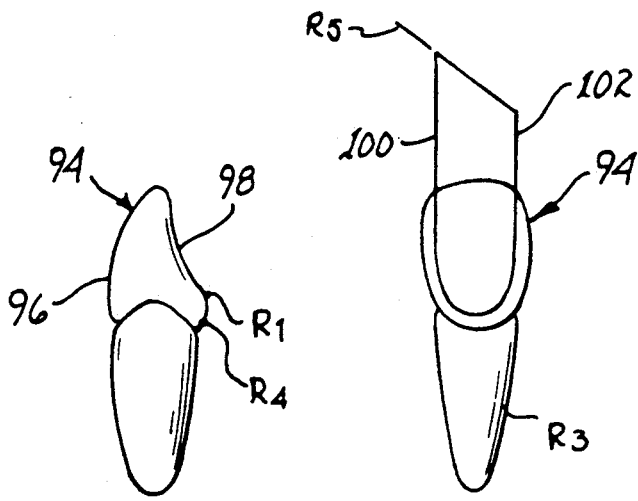
FIGS. 10a and 10b illustrate representative side and rear elevational views of premolar and anterior crowns mounted upon a tooth.

To assist a dentist in extracting teeth, numerous extraction forceps have been developed for groups of teeth which represent similar or related accessibility, direction of extraction and manipulation impediments. These forceps can generally be categorized as being suitable for anterior, premolar or molar teeth. It is to be understood that further gradations also exist. As shown in plan view in FIG. 1, a generalized pair of forceps 10 includes handles 12,14 pivotally attached to one another by pivot means 16. Jaws 18,20 associated with handles 12,14, respectively, may extend generally planar with the handles or may be slightly bent, as shown in side view in FIG. 2 or substantially bent as shown in side view in FIG. 3. The degree of bend of jaws 18,20 primarily dictates the type of tooth with which the pair of forceps is to be used.

For tooth extraction purposes, jaws 18,20 are of surgical steel or similar material which permits a very firm rigid grip of a tooth to be extracted. Various composite plastic materials can also be used. Whether the act of gripping and manipulating the tooth during extraction results in damage to the tooth enamel or the structure of the tooth is generally not of significance.

When a crown is to be removed in the event the seal for the crown has been compromised or the crown needs to be repaired or adjusted, it is important to prevent damage to the crown during the act of removal. Were such damage to occur, reconstruction or replacement of the crown would result in substantial expense which should be avoided. Because of the fragility of crowns, a dentist often must rely upon the strength of his fingers to effect removal since implements for this purpose and which have a low probability of causing damage to the crown do not exist. All dentists do not have sufficient strength in their fingers to effect removal of a crown. Furthermore, the space or volume available within the oral cavity to manually grip a crown may be a limiting factor of the ease with which a crown can be removed by manual manipulation.

Since dental forceps have been developed to facilitate the grasp of any of a patient's teeth, and as a crown usually has the same dimensions and configuration as the formerly existing complete tooth, the use of a pair of forceps intended for extraction of such tooth would vastly ease removal of the crown.

Referring to FIG. 4, there is illustrated a jaw 30, which jaw may be commensurate with one of jaws 18,20. The jaw has been formed with a depression 32 disposed in the working surface of the jaw. As shown in FIG. 5, an insert 34 includes a body portion 36 configured to mate with and be received within depression 32. To assist in removably installing the insert, a tang 38 may extend rearwardly. This tang is penetrably insertable into passageway 40 of the jaw to protrude therefrom. Upon grasping the protruding tang, insert 34 can be pulled, as well as pushed, into seated engagement with depression 32. Face 42 of the insert may extend peripherally beyond perimeter 44 of depression 32 to define a shoulder 46. The shoulder would rest upon and be supported by the surface of jaw 30 extending about perimeter 44. Moreover, face 42 is displaced from the surface of jaw 30 to the extent of the thickness of layer 48 adjacent body 36. Such displacement of the face will tend to preclude physical contact between jaw 30 and the crown to be removed whereby damage to the crown due to pressure exerted by the hard surface of jaw 30 would be precluded.

Insert 34 can be relatively easily removed from the supporting jaw by simply grasping the overhanging portion of layer 48 extending beyond the surface of the jaw and pulling the insert out of depression 32. Thereafter, the forceps may be autoclaved or otherwise sterilized without concern for damage to the insert. The pair of inserts usable with each pair of jaws may be rendered sterile by conventional techniques and packaged accordingly prior to use. It is contemplated that each pair of inserts would be disposable.

Preferably, insert 34 is of resilient flexible material, such as a rubber composition or a plastic composition, which is suitable for molding or other fabrication. Sufficient resistance to compressibility must be present to prevent the pressures exerted by a pair of jaws 30 (corresponding with each of jaws 18 and 20) from coming into contact with the crown to be removed. Furthermore, the product of the force vector times the frictional coefficient between the surfaces (insert/crown) prevents slippage without the application of sufficient compressive forces, which forces might collapse or otherwise damage the crown upon disengagement from the underlying and supporting tooth.

Referring to FIG. 6, there is illustrated a variant 60. This variant includes a sleeve 62 which may be slipped upon one of the jaws 30 (corresponding with each of jaws 18 and 20). A similar sleeve would be slipped upon the opposing jaw. The sleeve includes a bulbous element 64 of sufficient size to occupy cavity 32 of the sleeved jaw. That is, sufficient material must be present to essentially fill the cavity and prevent collapse of the sleeve adjacent the depression during manipulation of a crown.

In operation, the pair of forceps are manipulated to locate opposed bulbous elements 64 attendant the respective jaws adjacent the crown to be removed. Upon applying pressure to the crown, the bulbous elements will resiliently grip the crown and permit manipulation of the crown to effect its removal without damage to the surface of the crown or its underlying structure The use of sleeve 60, rather than insert 34 has an advantage in positioning stability. That is, insert 34 relies upon the support provided by the walls of depression 32 to retain the insert in place despite the disruptive forces that may occur during manipulation of the crown. Sleeve 60, on the other hand, can be configured to very tightly encircle the supporting jaw and thereby create frictional resistance against relative movement between the sleeve and the sleeved jaw. The physical engagement of bulbous element 64 with depression 32 in the jaw serves in the manner of a locking element to prevent rotation of the sleeve about its axis. It also serves in the manner of a locking element to inhibit axial translation of the sleeve.

FIG. 7a is a top view illustrating force vectors 66 imposed by insert 34 horizontally along the surface of the crown to be grasped. These vectors are essentially of equal length (equal force) due to the curved nature of the insert as dictated by the supporting jaw and further modified by the configuration of the insert to conform with the actual surface of the crown. Similarly, FIG. 7b is a side view illustrating force vectors 68 imposed by insert 34 vertically along the surface of the crown to be grasped. These vectors are essentially of equal length (equal force) due to the curved nature of the insert as dictated by the supporting jaw and further modified by the configuration of the insert to conform with the actual surface of the crown. The forces imposed are therefore uniform and little likelihood of distortion of the crown would exist.

Referring to FIG. 8, there is illustrated a prior art device having a pair of jaws 70,72 secured to a pliers type of device. Each of these jaws includes a cylindrical segment 74,76 of rigid material, such as stainless steel, faced with a resilient facing 78,80, respectively. The resilient facing provides a cushioning effect to a crown to be grasped. Because cylindrical segments 74,76 are generalized in terms of curvature, the forces imposed upon the crown to be removed are of greatest magnitude at the center of curvature, as shown in top view in FIG. 9a and as shown in side view in FIG. 9b with decreasing forces applied toward the opposed extremities. This is depicted by central vector 82 and lateral vector pairs 84,86 and 88,90. Thus, deformation of the crown to be removed is highly likely and such deformation may cause cracking or other damage to the porcelain of the crown and the underlying structure. It may be noted that the curvature of each of cylindrical segments 74,76 is about a single axis; there is no teaching for providing curvature about a second axis to produce a dished segment.

Figure 11:
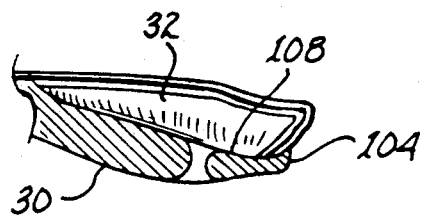
FIG. 11 illustrates a cross sectional view of a forceps jaw.

A representative tooth mounted premolar and anterior crown 94 is illustrated in FIGS. 10a and 10b. Outward surface 96 is generally referred to as the labial surface while inward surface 98 is referred to as the lingual surface. These are the two surfaces contacted by the jaws of the forceps during extraction. Furthermore, it is generally sixty percent of these surfaces which is gripped. This portion of the lingual surface is identified by lines 100,102 (the cavity rim associated with radius R5 (FIG. 11). To promote and ensure a non slipping grip, the forceps jaws preferably conform with the various curvatures depicted by designations R1, R2, R3, R4 and R5 in the cervical, mid and incisal portions of the crown.

FIG. 11 illustrates a cross section of a typical depression 32 (see FIGS. 4 and 5) formed in a jaw 30. The depression illustrated is representative of the curvature of the lingual surface 98, it being understood that the curvature of the depression used in conjunction with the labial surface 96 would be commensurately configured. More particularly, the curvature or radius at each of locations R1, R2, R3, R4 and R5 would be specifically contoured to the mating curvature of the crown. That is, R1 would be equivalent with the lower lingual profile, R2 would be equivalent to the upper lingual profile, R3 would be equivalent to the cavity sidewall, R4 would be equivalent to the tooth gum line in the cervical area and R5 would be equivalent to the curvature of the rim of the depression commensurate with the contact area of the lingual surface extending longitudinally along the tooth generally proximate lines 100,102 (see FIG. 10b).

Figure 12A:
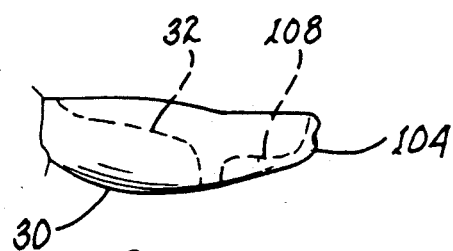
FIGS. 12a, 12b and 12c illustrate cross sectional views of the jaw segment illustrated in FIG. 11.
Figure 12C:
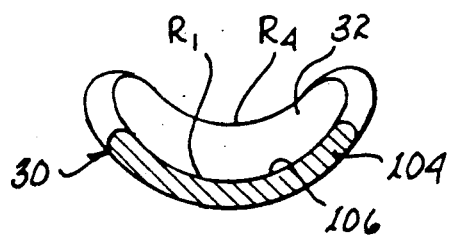
Figure 12B:
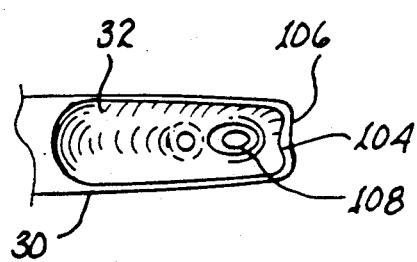

Referring jointly to FIGS. 12a, 12b and 12c, further views of depression 32 in jaw 30 are illustrated. Terminal end 104 includes a curved edge 106 conforming in general to the curvature attendant R1 of crown 94. A dished section 108 is configured to receivingly mate with the bulbous like cervical lingual surface of crown 94. The remaining curvatures and contours of depression 30 generally conform to the profiles contained in the tooth surfaces within lines 100,102 (FIG. 10b).

The insert to be fitted within the jaw and its depression depicted in FIG. 11 and in FIGS. 12a, 12b and 12c will compressingly conform with the depression to receive the commensurate lingual or labial surface of a crown and exert uniform forces thereagainst upon gripping of the crown by the forceps. Such uniformity of gripping forces along the surface contacted will reduce stress concentrations to minimize damage or deformation to the crown, and minimize the likelihood of slipping while providing a high degree of control to manipulation of the crown during extraction.

Figure 13A:
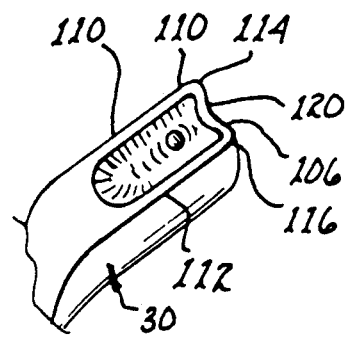
FIGS. 13a and 13b illustrate modifications to the jaw for accommodating cervical ridge anomalies.
Figure 13B:
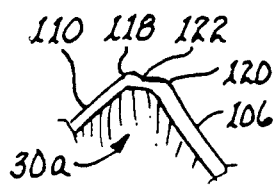

FIGS. 13a and 13b partially illustrate a variant 30a of jaw 30 for accommodating anomalies of the dental prosthetic to be removed. In jaw 30, edges 110,112 join with terminal edge 106 at locations which define relatively sharp points 114,116. Depending upon the structure and configuration of both the tooth and the associated dental prosthetic, there may be anomalies in the area of the cervical ridge and primarily in the mesio/distal length. The presence of sharp points 114,116 on jaw 30 may create difficulties in effecting facile gripping and removal of the dental prosthetic. To eliminate such cause for difficulty, variant jaw 30a may be used. In the area of one of the pair of sharp points identified within circle 130 in FIG. 13a, segments of edges 110,106 extending from the junction to locations identified by 118,120 are removed. The resulting edge, identified by numeral 122 in FIG. 13b, eliminates point 114 present in jaw 30. A similar modification is performed on edges 112,106 forming point 116 to replace this point with an edge equivalent to edge 122. Such modification to jaw 30 will not negatively affect the efficacy of edge 106 in engaging the cervical ridge of the dental prosthetic as a functional equivalent of a dentist's fingernail and it will accommodate the aforementioned possible anomalies.

While the principles of the invention have now been made clear in an illustrative embodiment, there will be immediately obvious to those skilled in the art many modifications of structure, arrangement, proportions, elements, materials and components used in the practice of the invention which are particularly adapted for specific environments and operating requirements without departing from those principles.

We claim:

1. A pair of forceps for gripping in a non damaging manner a dental prosthetic device to effect removal of the dental prosthetic device, said pair of forceps comprising in combination:

(a) a pair of handles for manipulating said pair of forceps;

(b) a pair of jaws for gripping opposed side of the dental prosthetic device, one end of each handle of said pair of handles including one jaw of said pair of jaws;

(c) means for pivotally interconnecting said pair of handles to relocate said pair of jaws toward and away from one another in response to pivotal movement of said pair of handles relative to one another, said pair of jaws being located and movable outside of a plane defined by the pivotal movement of said pair of handles;

(d) at least one jaw of said pair of jaws including a cavity and a perimeter defining said cavity, said perimeter including an indented edge segment for engaging the cervical ridge of the dental prosthetic, each said cavity being in opposed facing relationship to the other jaw of said pair of jaws, each said cavity including a surface defined by said perimeter which is three dimensionally compatible with the corresponding surface of the dental prosthetic device to be gripped; and (e) an insert demountably mountable within each of said cavities for contacting the dental prosthetic device and for restraining contact between the dental prosthetic device and the respective one of said perimeters.

2. The apparatus as set forth in claim 1 wherein the opposing jaw faces embody the geometric profiles of the labial and lingual surfaces of the prosthetic device to be removed.

3. The apparatus as set forth in claim 1 wherein each said insert includes means for transmitting relatively constant forces across the contact area of the dental prosthetic device due to the geometric profiles of their respective jaw cavities.

4. The apparatus as set forth in claim wherein each of said inserts is of resilient flexible material.

5. The apparatus as set forth in claim 1 wherein each of said inserts is sufficiently compressible to conform with the surface of the dental prosthetic device in contact with said insert while exerting essentially uniform forces across the surface contacted.

6. The apparatus as set forth in claim 1 wherein at least one of said inserts extends beyond said perimeter of the respective one of said cavities.

7. The apparatus as set forth in claim 1 wherein at least one of said cavities includes a passageway extending through the respective one of said jaws.

8. The apparatus as set forth in claim 7 wherein at least one of said inserts includes a tang for penetrably engaging said passageway.

9. The apparatus as set forth in claim 1 wherein each of said cavities is elongated in the direction of the longitudinal axis of the respective one of said pair of jaws.

10. The apparatus as set forth in claim 1 wherein said insert includes a sleeve for receiving a segment of the respective jaw of said pair of jaws.

11. The apparatus as set forth in claim 1 wherein the longitudinal axis of each jaw of said pair of jaws is at an angle of approximately 45° with respect to the respective one of said pair of handles.

12. The apparatus as set forth in claim 1 wherein the longitudinal axis of each jaw of said pair of jaws is at an angle of substantially more than 45° with respect to the respective one of said pair of handles.

13. A pair of forceps for gripping in a non damaging manner a dental prosthetic device to effect removal of the dental prosthetic device, said pair of forceps comprising in combination:

(a) a pair of handles for manipulating said pair of forceps;

(b) a pair of jaws for gripping opposed side of the dental prosthetic device, one end of each handle of said pair of handles including one jaw of said pair of jaws;

(c) means for pivotally interconnecting said pair of handles to relocate said pair of jaws toward and away from one another in response to pivotal movement of said pair of handles relative to one another, said pair of jaws being located and movable outside of a plane defined by the pivotal movement of said pair of handles;

(d) at least one jaw of said pair of jaws including a cavity and a perimeter defining said cavity, each said cavity being in opposed facing relationship to the other jaw of said pair of jaws; and (e) an insert demountably mountable within each of said cavities for contacting the dental prosthetic device and for restraining contact between the dental prosthetic device and the perimeter, said insert including a sleeve for receiving a segment of the respective jaw of said pair of jaws and a bulbous element for engaging said cavity of the respective jaw of said pair of jaws.

14. A pair of forceps for gripping in a non damaging manner a dental prosthetic device having a cervical ridge to effect removal of the dental prosthetic device, said pair of forceps including a pair of handles supporting jaws for gripping opposed labial and lingual surfaces of the dental prosthetic device, said pair of forceps comprising in combination:

(a) a first cavity formed in one jaw of the pair of jaws and generally conforming in configuration with one of the labial and lingual surfaces of the dental prosthetic device to be removed;

(b) a second cavity formed in the other jaw of the pair of jaws and generally conforming in configuration with the other of the labial and lingual surfaces of the dental prosthetic device to be removed, said second cavity being oriented in opposing relationship to said first cavity;

(c) a first perimeter for defining the edge of said first cavity, said first perimeter including an inwardly curved edge segment for engaging a section of the cervical ridge of the dental prosthetic device;

(d) a second perimeter for defining the edge of said second cavity, said second perimeter including a further inwardly curved edge segment for engaging a further section of the cervical ridge of the dental prosthetic device; and (e) first and second inserts disposed within said first and second cavities, respectively, for bearing against the corresponding labial and lingual surfaces to grip the dental prosthetic and effect removal of the dental prosthetic device upon manipulation of said pair of forceps.

15. The apparatus as set forth in claim 14 wherein said first and second inserts are of resilient material.

16. The apparatus as set forth in claim 14 including means for removably securing said first and second inserts within the respective first and second cavities.

* * * * *